(12) United States Patent
Stark et al.

(10) Patent No.: US 7,940,258 B2
(45) Date of Patent: May 10, 2011

(54) AUTOMATIC ADJUSTMENT OF AN ORTHODONTIC BRACKET TO A DESIRED MESIO-DISTAL POSITION WITHIN A THREE-DIMENSIONAL (3D) ENVIRONMENT

(75) Inventors: Nicholas A. Stark, Cottage Grove, MN (US); Richard E. Raby, North St. Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 701 days.

(21) Appl. No.: 11/279,183

(22) Filed: Apr. 10, 2006

(65) Prior Publication Data

US 2007/0238064 A1    Oct. 11, 2007

(51) Int. Cl.
*G06T 19/20* (2006.01)
(52) U.S. Cl. ............... 345/419; 345/420; 700/98
(58) Field of Classification Search ............ 433/24; 345/419, 420; 700/98
See application file for complete search history.

(56) References Cited

U.S. PATENT DOCUMENTS

| | | | |
|---|---|---|---|
| 5,368,478 A * | 11/1994 | Andreiko et al. ............... 433/24 |
| 5,871,350 A | 2/1999 | Clark et al. |
| 5,879,158 A | 3/1999 | Doyle et al. |
| 6,099,314 A | 8/2000 | Kopelman et al. |
| 6,123,544 A | 9/2000 | Cleary |
| 6,152,731 A | 11/2000 | Jordan et al. |
| 6,322,359 B1 | 11/2001 | Jordan et al. |
| 6,334,772 B1 | 1/2002 | Taub et al. |
| 6,334,853 B1 | 1/2002 | Kopelman et al. |
| 6,457,978 B1 | 10/2002 | Cloonan et al. |
| 6,565,355 B2 | 5/2003 | Kim et al. |
| 6,616,444 B2 | 9/2003 | Andreiko et al. |
| 6,632,089 B2 * | 10/2003 | Rubbert et al. ............... 433/24 |
| 6,664,986 B1 | 12/2003 | Kopelman et al. |
| 6,688,885 B1 * | 2/2004 | Sachdeva et al. ............... 433/24 |
| 6,695,613 B2 | 2/2004 | Taub et al. |
| 6,697,164 B1 | 2/2004 | Babayoff et al. |
| 6,739,869 B1 | 5/2004 | Taub et al. |
| 7,155,373 B2 * | 12/2006 | Jordan et al. ............... 703/1 |
| 2002/0025503 A1 | 2/2002 | Chapoulaud et al. |
| 2002/0055081 A1 * | 5/2002 | Hughes et al. ............... 433/24 |
| 2003/0096210 A1 * | 5/2003 | Rubbert et al. ............... 433/24 |
| 2003/0143509 A1 * | 7/2003 | Kopelman et al. ............... 433/24 |
| 2003/0215764 A1 | 11/2003 | Kopelman et al. |
| 2003/0219692 A1 | 11/2003 | Kopelman et al. |
| 2003/0224312 A1 | 12/2003 | Bergersen |
| 2003/0224316 A1 | 12/2003 | Marshall |
| 2004/0115586 A1 | 6/2004 | Andreiko |
| 2004/0142298 A1 | 7/2004 | Taub et al. |
| 2004/0214128 A1 * | 10/2004 | Sachdeva et al. ............... 433/24 |
| 2005/0130095 A1 | 6/2005 | Raby et al. |
| 2005/0170309 A1 | 8/2005 | Raby et al. |
| 2005/0191593 A1 | 9/2005 | Knopp |
| 2006/0024637 A1 | 2/2006 | Raby et al. |
| 2006/0073435 A1 | 4/2006 | Stark et al. |
| 2006/0073436 A1 | 4/2006 | Raby et al. |
| 2006/0147872 A1 * | 7/2006 | Andreiko ............... 433/24 |

\* cited by examiner

*Primary Examiner* — Todd E Manahan
*Assistant Examiner* — Michael R Ballinger

(57) ABSTRACT

A system automatically adjusts an orthodontic bracket to a desired mesio-distal position on a tooth within a 3D environment. The system allows a practitioner to specify a desired mesio-distal position at which to place the bracket on the tooth. The practitioner may choose the desired mesio-distal position from a standardized set of mesio-distal positions or may create a customized mesio-distal position to meet a patient's particular needs. Based on the desired mesio-distal position, the system automatically adjusts the placement of the orthodontic bracket to the desired mesio-distal position on the tooth within the 3D environment. The system then generates a visual representation of the resulting bracket placement within the 3D environment.

42 Claims, 7 Drawing Sheets

AUTOMATIC ADJUSTMENT OF AN ORTHODONTIC BRACKET TO A DESIRED MESIO-DISTAL POSITION WITHIN A THREE-DIMENSIONAL (3D) ENVIRONMENT

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances, known as brackets, which are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly or torqued from one appliance to the next in accordance with the patient's malocclusion. However, the resiliency of the archwire tends to return the archwire to its normally curved shape that lies in the flat reference plane. As the archwire shifts toward the flat reference plane, the attached teeth are moved in a corresponding fashion toward an aligned, aesthetically pleasing array.

As can be appreciated, it is important for the practitioner using straight wire appliances to precisely fix each bracket in the proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal directions, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention relates to computer-implemented techniques for assisting practitioners in orthodontic diagnosis and treatment. More specifically, a computing system is described that provides an environment for modeling and depicting a three-dimensional (3D) representation of a patient's dental arch. By interacting with the system, orthodontic practitioners are able to visualize the 3D representation of the dental arch, and precisely position "virtual" orthodontic appliances relative to the modeled dental arch. For example, the orthodontic practitioner may interact with the system to position brackets on one or more teeth within the modeled dental arch.

As described in detail herein, the system allows the practitioner to pre-define a desired mesio-distal position at which a particular bracket is to be placed on a given tooth. The mesio-distal position may be defined as the distance from a bracket origin (e.g., the center of the base of the bracket slot) to both a distal-most point and mesial-most point on the tooth measured along the mesio-distal axis of the bracket. The desired mesio-distal position may be chosen from a standardized set of mesio-distal positions or may be customized by the practitioner to the particular needs of a patient, e.g., the practitioner may specify a mesio-distal offset from the center of the mesio-distal axis.

Based on the defined mesio-distal position, the computing system executes software to automatically adjust and orient the virtual bracket within the 3D environment. Through a series of computational iterations, the system automatically adjusts the mesio-distal position of the virtual bracket until the mesio-distal position closely approximates the desired mesio-distal position. In some embodiments, the system may eliminate portions of the 3D modeling data and surface structure of the virtual tooth to more accurately center the bracket on the facial surface of the tooth. For example, the system may eliminate 3D data associated with a lingual surface or certain lingual protrusions of the tooth in order to more accurately position the bracket in a mesio-distal position on the facial surface of the tooth.

Once the updated mesio-distal location and orientation of the bracket have been computed, the system visually represents the resulting bracket placement within the 3D environment. The automatic bracket adjustment and the visual representation aid the practitioner in achieving the desired bracket placement on the tooth.

In one embodiment, the invention is directed to a method comprising rendering a digital representation of at least a portion of a tooth within a three-dimensional (3D) environment, receiving a desired mesio-distal position for an orthodontic appliance associated with the tooth, and automatically adjusting the orthodontic appliance to the desired mesio-distal position on the tooth within the 3D environment.

In another embodiment, the invention is directed to a system comprising a computing device and modeling software executing on the computing device. The modeling software comprises a rendering engine that renders a digital representation of at least a portion of a tooth within a three-dimensional (3D) environment, and a mesio-distal position control module that automatically adjusts an orthodontic appliance to a desired mesio-distal position on the tooth within the 3D environment.

In another embodiment, the invention is directed to a computer-readable medium containing instructions. The instructions cause a programmable processor to render a digital representation of at least a portion of a tooth within a three-dimensional (3D) environment, receive a desired mesio-distal position for an orthodontic appliance associated with the tooth, and automatically adjust the orthodontic appliance to the desired mesio-distal position on the tooth within the 3D environment.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
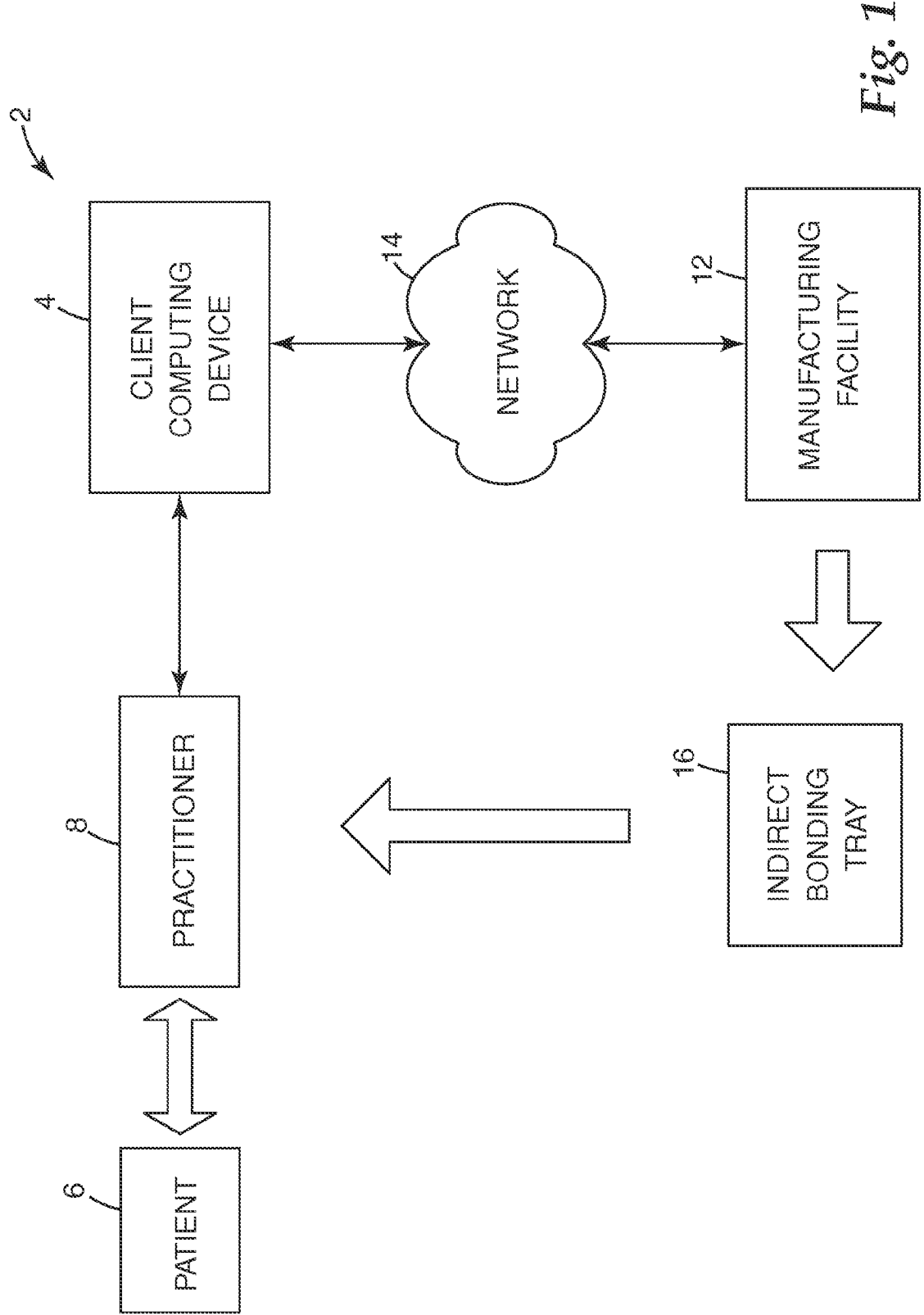
FIG. 1 is a block diagram illustrating an exemplary computer environment in which a client computing device presents an environment for modeling a three-dimensional (3D) representation of a dental arch of a patient.

FIG. 1 is a block diagram illustrating an exemplary computer environment 2 in which a client computing device 4 presents an environment for modeling a three-dimensional (3D) representation of a dental arch of a patient 6. In this example, an orthodontic practitioner 8 interacts with modeling software executing on client computer device 4 to visualize the 3D representation of the dental arch, and precisely position "virtual" appliances (e.g., brackets) on individual teeth within the modeled dental arch.

The 3D representation of the dental arch may be initially generated by digitally scanning a physical dental impression of the teeth of patient 6 or by scanning a casting made from the impression. Alternatively, practitioner 8 may use an intraoral scanner to produce the 3D digital representation directly from the teeth of patient 6. Other methods of scanning could also be used, and the invention should not be limited to the methods described above. Practitioner 8 may interact with the modeling software to view the 3D digital representation of the teeth and to ultimately approve the point on each tooth where the respective bracket is to be located. During this process, the modeling software manipulates each bracket as a separate object within the 3D environment and fixes the position of each bracket within the 3D space relative to a coordinate system associated with the modeled tooth upon which the virtual bracket resides. Consequently, practitioner 8 may independently view and approve the precise location of each bracket within the 3D environment relative to its respective tooth.

Although the description will generally discuss the display and positioning of orthodontic brackets, it shall be understood that client computing device 4 may display and/or position any type of orthodontic appliance without departing from the scope of the present invention. Examples of such orthodontic appliances include orthodontic brackets, buccal tubes, sheaths, buttons or archwires. In addition, client computing device 4 need not display a full visual representation of the appliance. Rather, a portion of the appliance may be displayed. As another alternative, client computing device 4 need not display the appliance itself. Rather, another object or graphical icon associated with an appliance or with the placement of an appliance may be shown instead of or in addition to the appliance itself. Examples of such other objects include crosshairs (intersecting lines indicating the position on a tooth where the center of an appliance is to be placed), placement jigs, placement guides, or other peripherals which may represent or be attached to an appliance, or which may be otherwise associated with an appliance and/or its placement. The term "appliance" as used herein shall therefore be understood to include any type of appliance, a full or partial representation of an appliance, or any object associated with an appliance and/or its placement.

Client computing device 4 may show a digital representation of an entire dental arch, a portion of a dental arch, an individual tooth within the dental arch, a portion of a tooth within the dental arch, or some combination thereof for viewing by practitioner 8. Client computing device 4 may also show a digital representation of appliances on all of the teeth in a dental arch, the appliances on a portion of the teeth in a dental arch, an appliance on a single tooth, or an appliance on a portion of a tooth. Similarly, client computing device 4 may show a digital representation of an entire appliance, a portion of an appliance, or simply the crosshairs of an appliance (which may indicate, for example, the location on a tooth where the center of the appliance is to be placed). It shall be understood, therefore, that the image presented to the practitioner 8 by client computing device 4 may take many different forms, and that the invention is not limited in this respect.

As described in detail herein, the modeling software automatically adjusts an orthodontic bracket to a desired mesio-distal position on a tooth within the 3D environment. The brackets may initially be placed in the 3D environment using the method described in copending and commonly assigned US Publication No. 2005/0130095, entitled "Method Of Orienting An Orthodontic Appliance To A Tooth", to Raby, et al., which is incorporated herein by reference in its entirety. Manual adjustment of orthodontic brackets may be assisted by use of visual planar guides, as described in copending and commonly assigned US Publication No. 2005/0170309, entitled "Planar Guides to Visually Aid Orthodontic Appliance Placement within a Three-Dimensional (3D) Environment", to Raby, et al., which is incorporated herein by reference in its entirety. In that application, a system visually aids the user in manual placement of brackets through manual adjustments to bracket position and orientation.

Moreover, the brackets may also be automatically adjusted to a desired occlusal height on the tooth within the 3D environment either prior or subsequent to the mesio-distal positioning described herein using the techniques described in US Publication No. 2006/0024637, entitled "Automatic Adjustment of an Orthodontic Bracket to a Desired Occlusal Height within a Three-Dimensional (3D) Environment", to Raby, et al., which is incorporated herein by reference in its entirety.

In accordance with the techniques described herein, the modeling software automatically adjusts an orthodontic bracket within the 3D environment to a desired mesio-distal position on a tooth while simultaneously maintaining a desired fit between the bracket base and the tooth. In some embodiments, the practitioner specifies a desired mesio-distal position at which the bracket is to be placed. Based on this desired mesio-distal position, the modeling software automatically adjusts the placement of the orthodontic bracket to the desired mesio-distal position on the tooth within the 3D environment while maintaining the desired fit.

Once the brackets are placed and the practitioner has indicated his or her approval, client computing device 4 communicates the bracket placement positions to manufacturing facility 12 via network 14. In response, manufacturing facility 12 constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Figure 2:
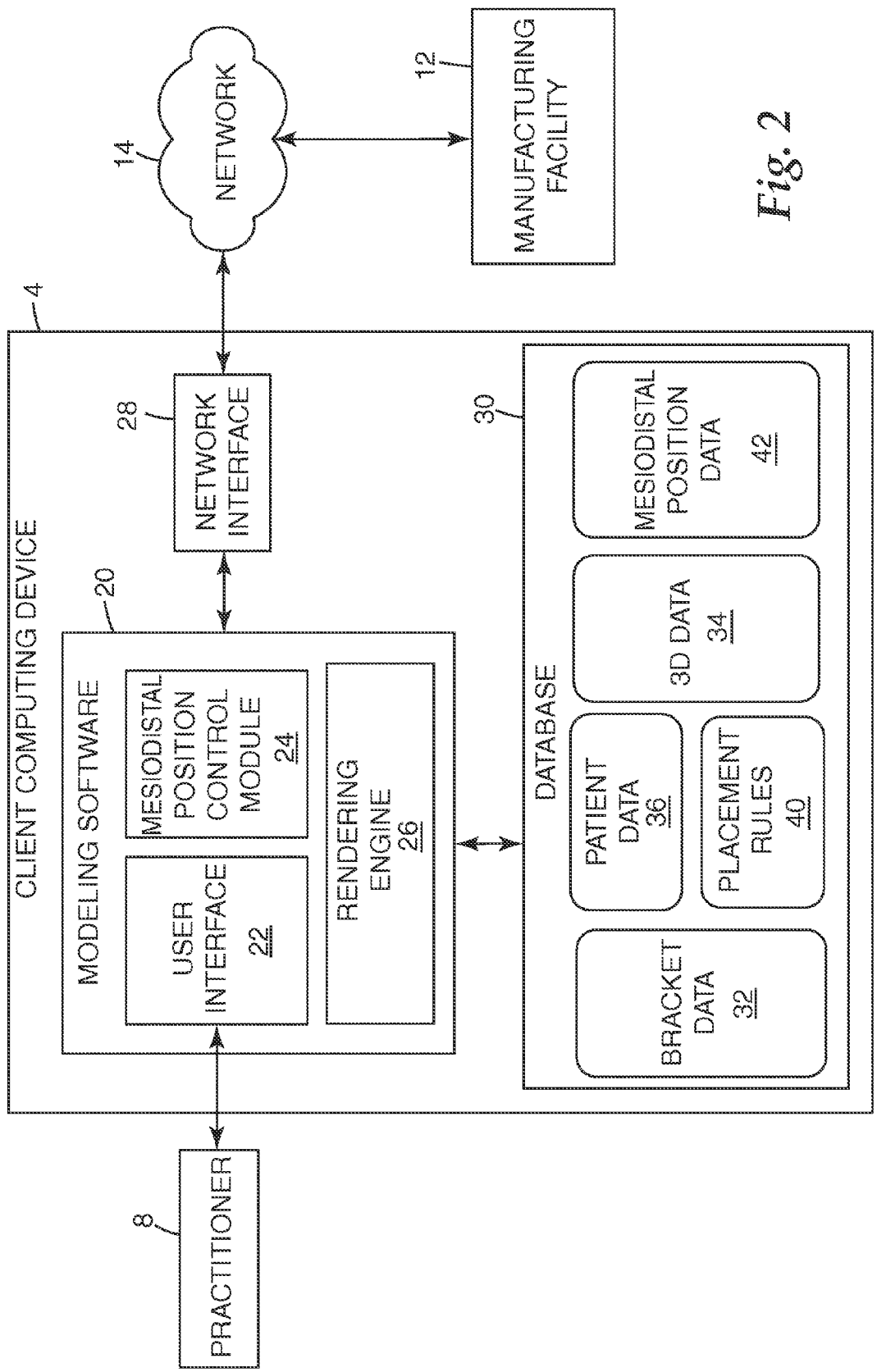
FIG. 2 is a block diagram illustrating an example embodiment of a client computing device in further detail.

FIG. 2 is a block diagram illustrating an example embodiment of a client computing device 4 in further detail. In the illustrated embodiment, client computing device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, a mesio-distal position control module 24, and a rendering engine 26.

User interface 22 provides a graphical user interface (GUI) that visually displays the 3D representation of the patient's teeth as well as 3D representations of the brackets. In addition, user interface 22 provides an interface for receiving input from practitioner 8, e.g., via a keyboard and a pointing device, for manipulating the brackets and placing the brackets on respective teeth within the modeled dental arch.

Modeling software 20 interacts with database 30 to access a variety of data, such as bracket data 32, 3D data 34, patient data 36, placement rules 40 and mesio-distal position data 42. Database 30 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS) or object relational (ORDBMS) database management system. The data may, for example, be stored within a single relational database, such as SQL Server from Microsoft Corporation. Although illustrated as local to client computing device 4, database 30 may be located remote from the client computing device and coupled to the client computing device via a public or private network, e.g., network 14.

Modeling software 20, user interface 22, mesio-distal control module 24 and rendering engine 26 may comprise software instructions stored within a storage medium (e.g., disk, hard drive, solid state memory or the like) executable by one or more processors of client computing device 4.

Bracket data 32 describes a set of commercially available brackets that may be selected by practitioner 8 and positioned within the 3D modeling environment. For example, bracket data 32 may store a variety of attributes for the commercially available brackets, such as dimensions, slot locations and characteristics, torque angles, angulations and other attributes. User interface 22 provides a menu-driven interface by which practitioner 8 selects the type of brackets for use in defining an orthodontic prescription for patient 6.

Patient data 36 describes a set of one or more patients, e.g., patient 6, associated with practitioner 8. For example, patient data 36 specifies general information, such as a name, birth date, and a dental history, for each patient. In addition, patient data 36 specifies a current prescription specified for each of the patients, including the types of brackets selected by practitioner 8 for use with each of the patients.

Mesio-distal position data 42 specifies a set of mesio-distal positions and may be provided as default positions specified by libraries of virtual representations of industry-standard brackets. In addition, practitioner 8 may customize the default mesio-distal positions or specify new positions, for example, via user interface 22 for one or more teeth in the dentition. Mesio-distal position is one aspect of a patient's orthodontic prescription and, in one embodiment, is defined as the distance from the bracket origin (the center of the base of the bracket slot) to the mesial-most and distal-most points on the tooth, measured in the bracket slot coordinate system along the mesio-distal axis. Other definitions may readily be used. For example, the bracket origin may be defined as the mesial-most point of the bracket slot, the distal-most point of the bracket, or any other point of reference relative to the bracket. The prescribed mesio-distal position affects the resulting aesthetic appearance of the teeth.

The orthodontic industry has developed standard prescriptions for many commercially available orthodontic brackets. These standardized prescriptions generally include, among other aspects of a prescription, a set of mesio-distal positions that tend to satisfy the aesthetic requirements of most patients. Typically, a prescription specifies that the practitioner, such as practitioner 8, align the bracket so as to center the bracket along the mesio-distal axis of the tooth; however, the prescription may specify other positions offset from the center. Offset values typically comprise a few millimeters to either the mesial or distal direction along the center of this axis, such as a one millimeter distal offset or a two millimeter mesial offset from the center of the mesio-distal axis of the tooth. The standardized prescriptions may be used to achieve uniformity among patients or to avoid the more time consuming process of devising a custom set of mesio-distal positions for each tooth of an individual patient. User interface 22 may allow practitioner 8 to select one or more mesio-distal positions from the standardized prescriptions, and typically the practitioner selects a centered position along the mesio-distal axis.

With some patients, practitioner 8 may desire to create a customized set of mesio-distal positions to achieve a more aesthetically pleasing result, or to better take into account that patient's malocclusion. User interface 22 allows a practitioner to quantify the desired mesio-distal positions for each tooth as part of an overall prescription for a patient, whether the prescribed positions are customized or standardized. For some patients, a standardized set of mesio-distal positions for the teeth in the dentition may be satisfactory. Alternatively, practitioner 8 may create a customized set of mesio-distal positions for the teeth in the dentition by specifying mesio-distal offsets, as described above. As another example, a combination of standardized and customized mesio-distal positions throughout the dentition may be used. The desired mesio-distal positions are stored in database 30 as mesio-distal position data 42.

Modeling software 20 then iteratively adjusts the locations and orientations of the brackets within the 3D environment to the prescribed mesio-distal positions automatically, and stores the result in patient data 36. In particular, mesio-distal position control module 24 receives mesio-distal position data 42 and automatically and iteratively adjusts the mesio-distal positions of the brackets associated with each tooth until the desired mesio-distal positions specified by mesio-distal position data 42 are achieved within a degree of acceptable tolerance. During the process, mesio-distal position control module 24 maintains a fit between the bracket base and the surface of the tooth.

Placement rules 40 may specify industry-defined placement rules for commercially available brackets. In addition, placement rules 40 may include user-defined rules specified by practitioner 8 or other rules for controlling bracket placement. For example, one rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point). By automatically adjusting the bracket to a specified mesio-distal position, modeling software 20 may allow the practitioner 8 to place the orthodontic appliance on the tooth so that certain placement rules are satisfied.

As another example, practitioner 8 may desire to place a bracket at a mesio-distal position that is different from the FA Point. Consequently, practitioner 8 may specify different mesio-distal positions for different types of teeth in the dentition, for different types of brackets, for different customized prescriptions, or for combinations thereof. Optionally, the desired mesio-distal position may be based in whole or in part on known rules associated with a particular type, or prescription, of the appliances selected by practitioner 8.

Rendering engine 26 accesses and renders 3D data 34 to generate the 3D view presented to practitioner 8 by user interface 22. More specifically, 3D data 34 includes information defining the 3D objects that represent each tooth and bracket within the 3D environment. Rendering engine 26 processes each object to render a 3D triangular mesh surface based on a viewing perspective of practitioner 8 within the 3D environment. User interface 22 displays the rendered 3D triangular mesh to practitioner 8, and allows the practitioner to change viewing perspectives and manipulate objects within the 3D environment.

Figure 3:
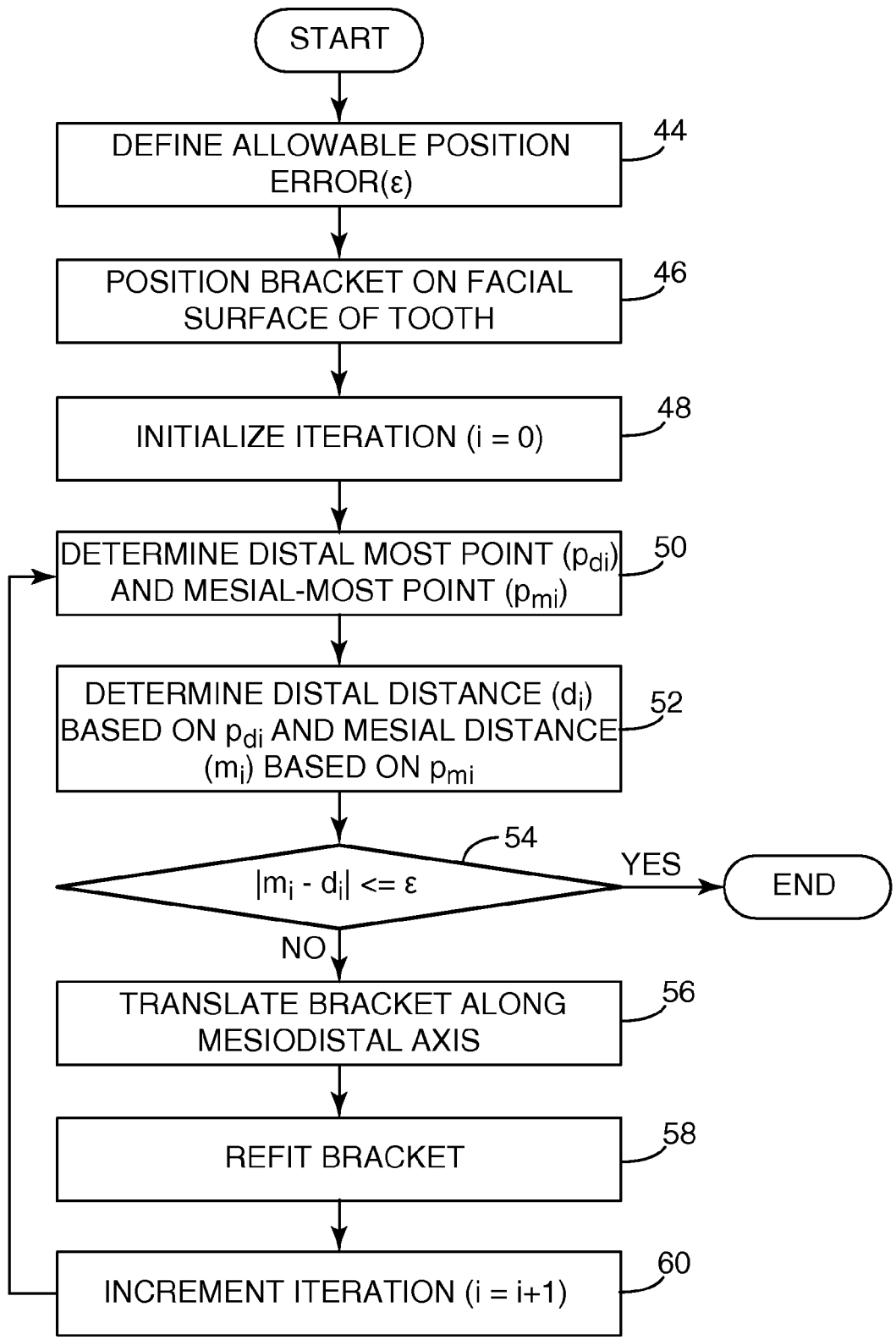
FIG. 3 is a flowchart illustrating one example method of automatically adjusting an orthodontic bracket to a desired mesio-distal position on a tooth.

FIG. 3 is a flowchart illustrating one exemplary method of automatically adjusting an orthodontic bracket to a desired mesio-distal position on a tooth within a 3D virtual environment. More specifically, the flowchart of FIG. 3 illustrates operation of mesio-distal control module 24 in automatically adjusting an orthodontic bracket within the 3D virtual environment to locate, orient and fit the bracket on a surface of a virtual representation of a tooth. The method shown in FIG. 3 may be used on anterior teeth (incisor or cuspid) as well as on posterior teeth (bicuspid or molar) and is described below in reference to FIGS. 4A-4G.

In general, FIGS. 4A-4G illustrate the method discussed above by which a client computing device, such as client computing device 4 of FIG. 2, automatically adjusts the mesio-distal position of a virtual bracket upon a 3D representation of a tooth. While the method of FIG. 3 is described in reference to FIGS. 4A-4G, the method may be applied to any appliance, such as an orthodontic bracket, for automatic positioning to a desired mesio-distal location upon a surface of a virtual tooth. The method described below may follow or precede the automatic occlusal height adjustment of that same bracket, as described above, as automatic occlusal height adjustment may comprise a method independent or in conjunction with automatic mesio-distal positioning.

Figure 4A:
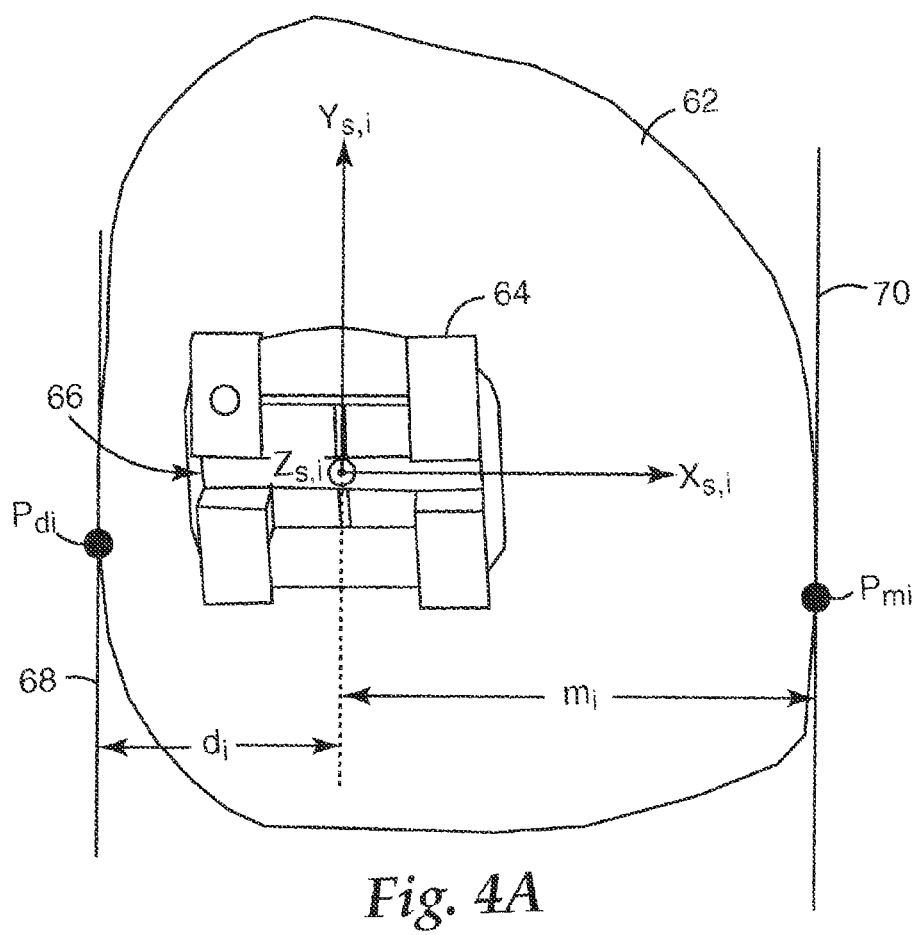
FIGS. 4A-4G illustrate the method by which a client computing device automatically adjusts the mesio-distal position of a virtual bracket upon a 3D representation of a tooth.
Figure 4B:
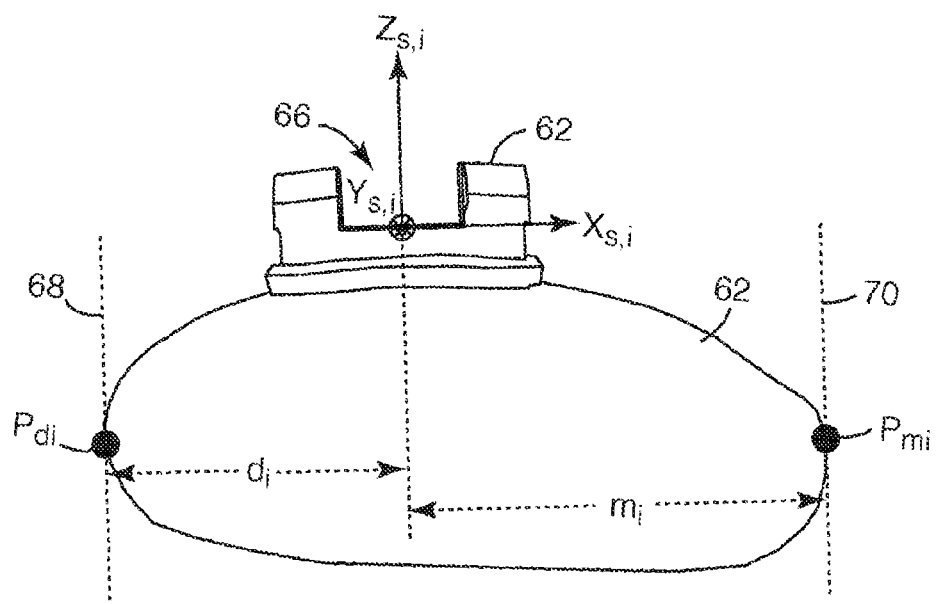

FIGS. 4A and 4B show respective facial and occlusal views of a 3D representation of a crown of an anterior tooth 62 with a virtual orthodontic bracket 64 whose base is in optimal contact with tooth 62. In both FIGS. 4A and 4B, the $x_{s,i}$, $y_{s,i}$, $z_{s,i}$ axes form the bracket slot coordinate system of bracket 64.

In this notation, "s" indicates the slot coordinate system and "i" indicates the iteration number through the automatic bracket adjustment process as performed by mesio-distal control module 24. Bracket 64 includes a slot 66 in which an archwire may be threaded to fix the bracket to the tooth. In one embodiment, the $x_{s,i}$ axis of the slot coordinate system is parallel to the slot 66 of bracket 64, as shown in FIG. 4A. In this embodiment, the $y_{s,i}$ axis is perpendicular to the $x_{s,i}$ axis (and therefore perpendicular to slot 66 of bracket 64), and the $z_{s,i}$ axis is perpendicular to the plane defined by the $y_{s,i}$ and $x_{s,i}$ axes.

Also, both slot 66 and the $x_{s,i}$ axis are perpendicular to distal-most plane 68 and mesial-most plane 70 of tooth 62. Distal-most plane 68 is defined as a plane perpendicular to the $x_{s,i}$ axis and intersecting the distal-most point $p_{di}$ of the crown of tooth 62 for a given iteration i. Similarly, mesial-most plane 70 is defined as a plane perpendicular to the $x_{s,i}$ axis and intersecting the mesial-most point $p_{mi}$ of the crown of tooth 62 for iteration i. For purposes of this example, distal distance ("$d_i$") is defined as the distance from distal-most plane 68 to the $y_{s,i}$ axis for iteration i, and mesial distance 78 ("$m_i$") is defined as the distance from mesial-most plane 70 to the $y_{s,i}$ axis for iteration i.

Referring again to the method of FIG. 3, a practitioner, such as practitioner 8, may initially interact with client computing device 4 (FIG. 2) to specify or select an allowable tolerance for any position error ($\epsilon$), which indicates the maximum allowable mesio-distal deviation from the desired mesio-distal position (44). Alternatively, the tolerance for any position error may be defined by modeling software 20 without requiring input from practitioner 8. Typical allowable position error values include $\frac{1}{1000}^{th}$ of an inch. Practitioner 8 may access patient data 36 to select or modify a prescription that indicates the desired appliance type, i.e., bracket 64, as well as the desired mesio-distal position, for each tooth in the dental arch.

Practitioner 8 then directs client computing device 4 via a keyboard, mouse, or other input device to position bracket 64 upon tooth 62 (46). In some cases, practitioner 8 may indicate an initial placement of bracket 64 via crosshairs or other such objects, as discussed above, and that placement may serve as an initial position for mesio-distal adjustment according to the process described below. Alternatively, the initial placement may be derived from a pre-defined standard or customized prescription selected by the practitioner 8 for the particular patient. Modeling software 20 may initially position bracket 64 using the method described in the above-referenced copending and commonly assigned U.S. Patent Application Publication No. 2005/0130095. Generally, U.S. Patent Application Publication No. 2005/0130095 describes a method of placing a bracket on a tooth to attain a close, mating fit between the base of the bracket and the tooth surface.

Once bracket 64 is placed within the 3D environment at an initial position of the facial surface of tooth 62, via either practitioner 8 or via modeling software 20, mesio-distal position control module 24 initializes the automatic mesio-distal adjustment process (48). In particular, upon receiving a request to automatically adjust the position of bracket 64, mesio-distal position control module 24 within client computing device 4 begins the automatic placement by initializing an iteration variable (i) to zero, or i=0, for the first time through the automatic adjustment process (46, FIG. 3).

Next, mesio-distal position control module 24 determines, for iteration i=0, distal-most point $p_{di}$ and mesial-most point $p_{mi}$ relative to the $x_{s,i}$ axis of the bracket slot coordinate system $x_{s,i}$, $y_{s,i}$, $z_{s,i}$ (50). In some embodiments, mesio-distal position control module 24 reduces the number of calculations per iteration, and potentially reduces the possibility for incorrect automatic adjustment, by eliminating some portions of the virtual surface structure of tooth 62 in order to more accurately calculate the mesial-most and distal-most points for each iteration. As one example, mesio-distal position control module 24 may eliminate points on the lingual surface, or non-facial surface, of tooth 62 in order to more accurately center bracket 64 to the facial surface instead of the entire tooth.

Regardless of whether point elimination occurs, mesio-distal position control module 24 determines the distal-most and mesial-most points during each iteration. In one approach, mesio-distal position control module 24 may translate all of the non-eliminated tooth points into bracket slot coordinate system $x_{s,i}$, $y_{s,i}$, $z_{s,i}$, sort the points according to their $x_{s,i}$ axis values, and assign the distal-most point and mesial-most point to the values having the largest positive and negative $x_{s,i}$ values, respectively. In other embodiments, mesio-distal position control module 24 may project all non-eliminated tooth points onto the $x_{s,i}$ axis of the bracket slot coordinate system and assign the distal-most point and mesial-most point to the values having the largest projected positive and negative $x_{s,i}$ values, respectively.

Inherent to calculating these points, mesio-distal position control module 24 also calculates distal-most plane 68 and mesial-most plane 70 by constructing both planes parallel to the $y_{s,i}$ axis and intersecting distal-most point $p_{di}$ and mesial-most point $p_{mi}$, respectively. After calculating planes 68, 70, mesio-distal position control module 24 determines, again for iteration i=0, distal distance $d_i$ based on distal-most point $p_{di}$ and mesial distance $m_i$ based on mesial-most point $p_{mi}$. More specifically, mesio-distal position control module 24 typically calculates distal distance $d_i$ and mesial distance $m_i$ by respectively calculating the length of a line drawn perpendicular to both the $y_{s,i}$ axis and distal-most plane 68 and the length of a line drawn perpendicular to both the $y_{s,i}$ axis and mesial-most plane 70.

Upon calculating distal distance $d_i$ and mesial distance $m_i$, mesio-distal position control module 24 determines whether the absolute value of the difference between distal distance $d_i$ and mesial distance $m_i$ is less than or equal to the allowable positional error $\epsilon$, as expressed mathematically by the equation: $|m_i-d_i|<=\epsilon$ (54). If this difference does not exceed the allowable positional error $\epsilon$, then bracket 64 need not be adjusted further, and the automatic mesio-distal adjustment process is finished ("YES" branch 54). However, if this difference exceeds the allowable positional error $\epsilon$, then further adjustment of bracket 64 is required ("NO" branch 54).

In instances where further adjustment is required, mesio-distal position control module 24 determines the bracket mesio-distal translation distance, i.e., the amount that the bracket should be moved along the mesio-distal axis based on the current mesial distance $m_i$ and distal distance $d_i$, and adjusts the location of bracket 64 within the 3D environment by the determined distance along the current mesio-distal axis $x_{s,i}$ (56). In some embodiments, mesio-distal position control module 24 determines the bracket mesio-distal translation distance based on further information, such as the desired mesio-distal position. For example, patient 6 may require bracket 64 to be placed at a mesio-distal position that is not centered on tooth 62, and this may be specified as a mesio-distal offset in patient data 36. Mesio-distal position control module 24 may access this offset within patient data 36 and vary its automatic mesio-distal adjustment property to compensate for this offset. Typically, mesio-distal position control module 24 determines which direction along the mesio-distal axis to translate and the distance to translate by subtracting the mesial distance $m_i$ from the distal distance $d_i$ and adjusting for any mesio-distal offset. For ease of illustration, it is assumed that no mesio-distal offset was specified or, in other words, that mesio-distal position control module 24 should center bracket 64 on the facial surface of tooth 62.

Figure 4C:
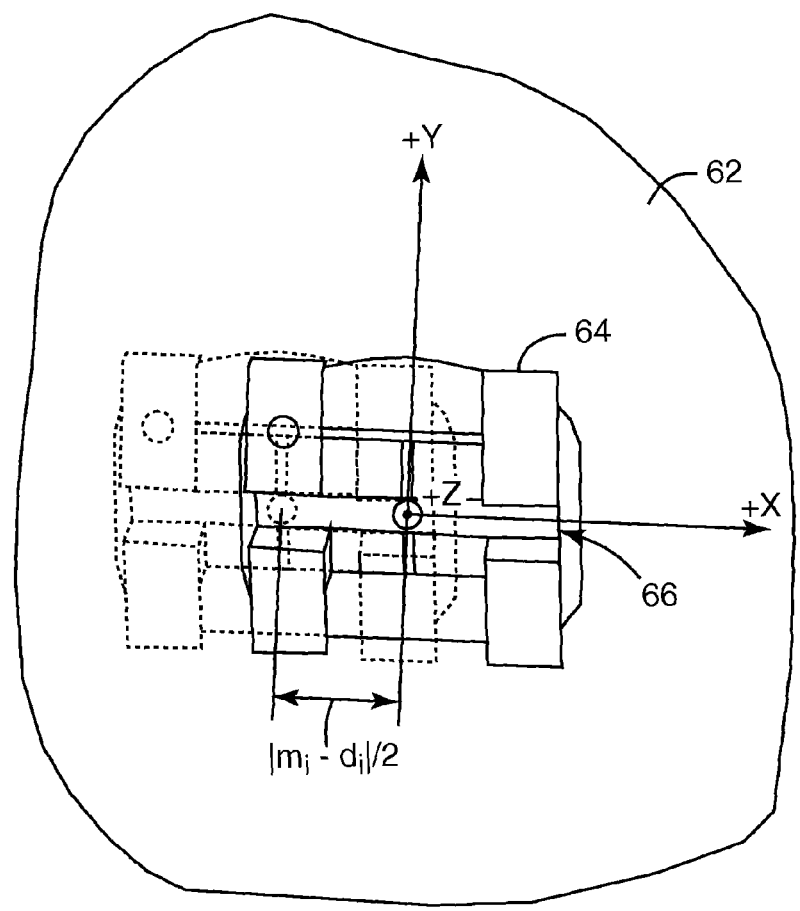
Figure 4D:
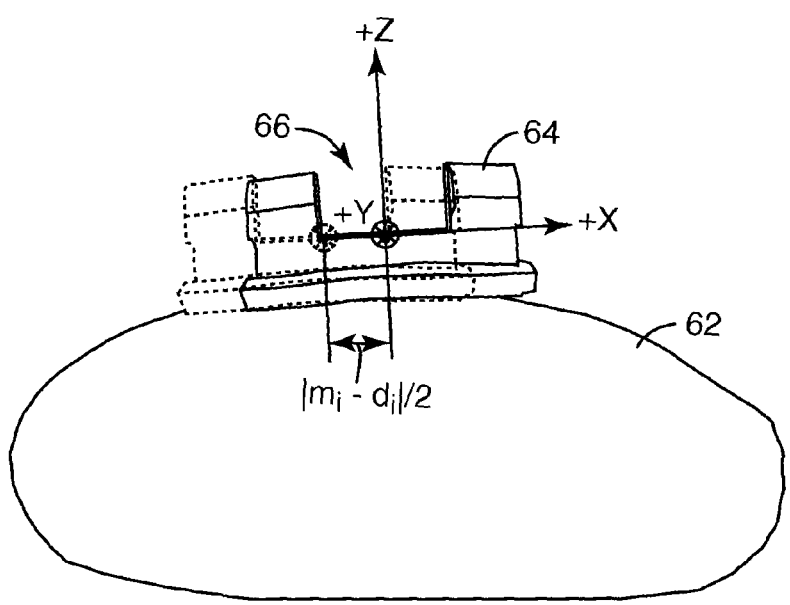

FIGS. 4C and 4D show facial and occlusal views, respectively, of the result of a first translation of bracket 64 along tooth 62. Both FIGS. 4C and 4D also show the previous location of bracket 64 as phantom (dashed) lines. In the illustrated example, mesio-distal position control module 24 translated bracket 64 by a distance of the absolute value of the difference between mesial distance $m_i$ and distal distance $d_i$ divided by two, which can be mathematically represented by the following equation: $|m_i-d_i|/2$. Further, mesio-distal position control module 24 translated bracket 64 mesially along the mesio-distal axis defined by the bracket slot coordinate system $x_{s,i}$, $y_{s,i}$, $z_{s,i}$.

Figure 4E:
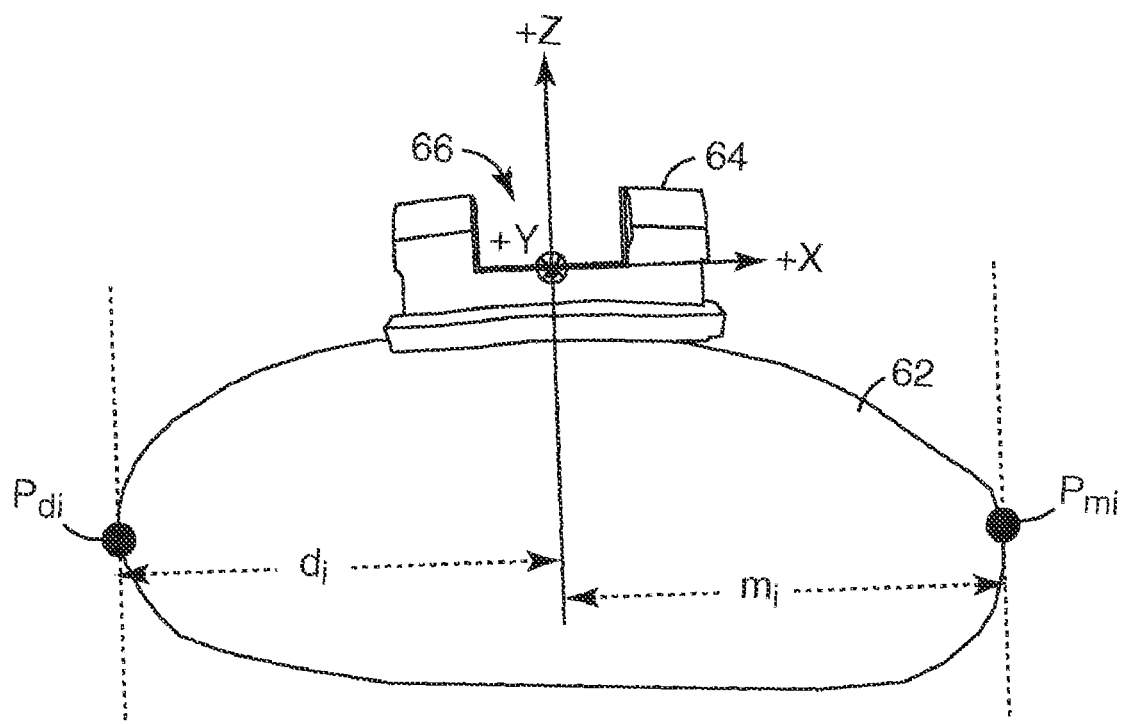

FIG. 4E shows another occlusal view of tooth 62 of FIG. 4A with bracket 64 translated after one or more iterations until reaching the desired mesio-distal point along the $x_{s,i}$ axis of the bracket slot coordinate system. In the illustrated example, mesial distance $m_i$ approximately equals distal distance $d_i$. However, after each translation, the base of bracket 64 may not maintain optimal contact with tooth 62. Assuming the prescription stored in patient data 36 specifies no mesio-distal offset, bracket 64 resides at the desired mesio-distal point, albeit without maintaining optimal contact with tooth 62.

Referring again to FIG. 3, mesio-distal position control module 24 may refit bracket 64 on tooth 62 after each translation in order to optimize contact between the base of bracket 64 and the facial surface of tooth 62 (58). One way to achieve this is to refit the bracket to achieve a close mating fit between the bracket and the tooth surface using the method described in U.S. patent application Ser. No. 10/734,323.

Figure 4F:
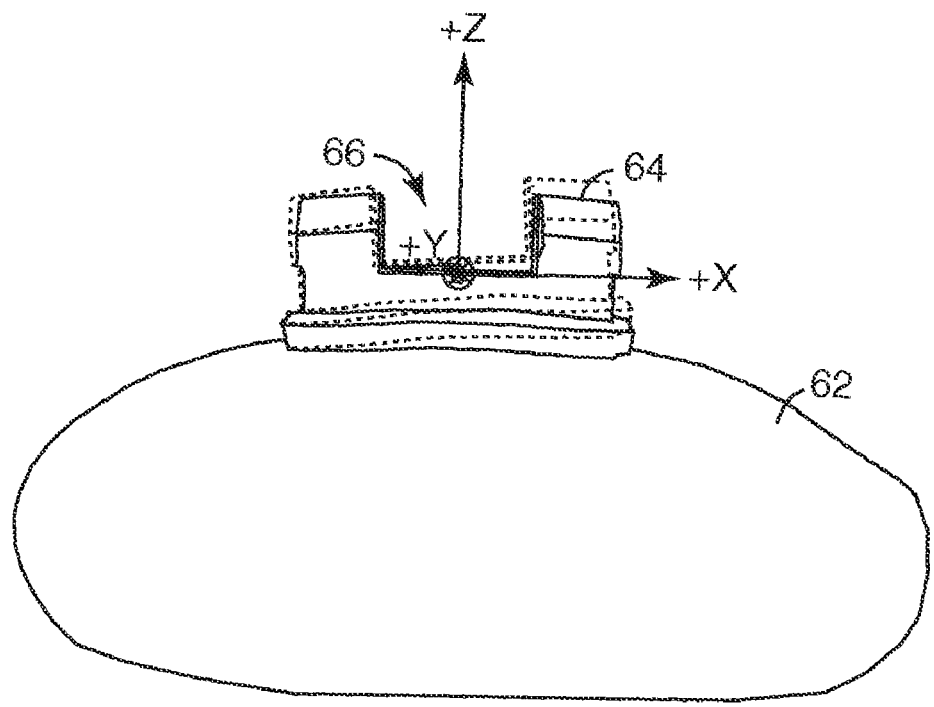

FIG. 4F shows an occlusal view of tooth 62 of FIG. 4A with bracket 64 positioned at the desired mesio-distal position after bracket 64 has been automatically refit to maintain optimal facial contact with tooth 62. Phantom (dashed) lines represent the previous position of bracket 64 and serves to illustrate the readjustment of bracket 64 resulting from the refit process.

Referring once again to FIG. 3, after refitting bracket 64, mesio-distal position control module 24 increments iteration i by one: i=i+1 (60). Upon incrementing iteration i, mesio-distal positioning module 24 repeats the process and again determines distal-most point $p_{di}$ and mesial-most point $p_{mi}$ for another iteration i, as described above (50). It may be necessary to re-determine these points because, during the refit process, bracket 64 may rotate, thereby rotating the reference, i.e., the bracket slot coordinate system, by which mesio-distal position control module 24 previously calculated distal-most point $d_0$ and mesial-most point $m_0$ for iteration i=0. Mesio-distal position control module 24 also determines distal distance $d_i$ based on distal-most point $p_{di}$ and mesial distance $m_i$ based on the mesial-most point $p_{mi}$ for the current iteration i, as described above (52).

Figure 4G:
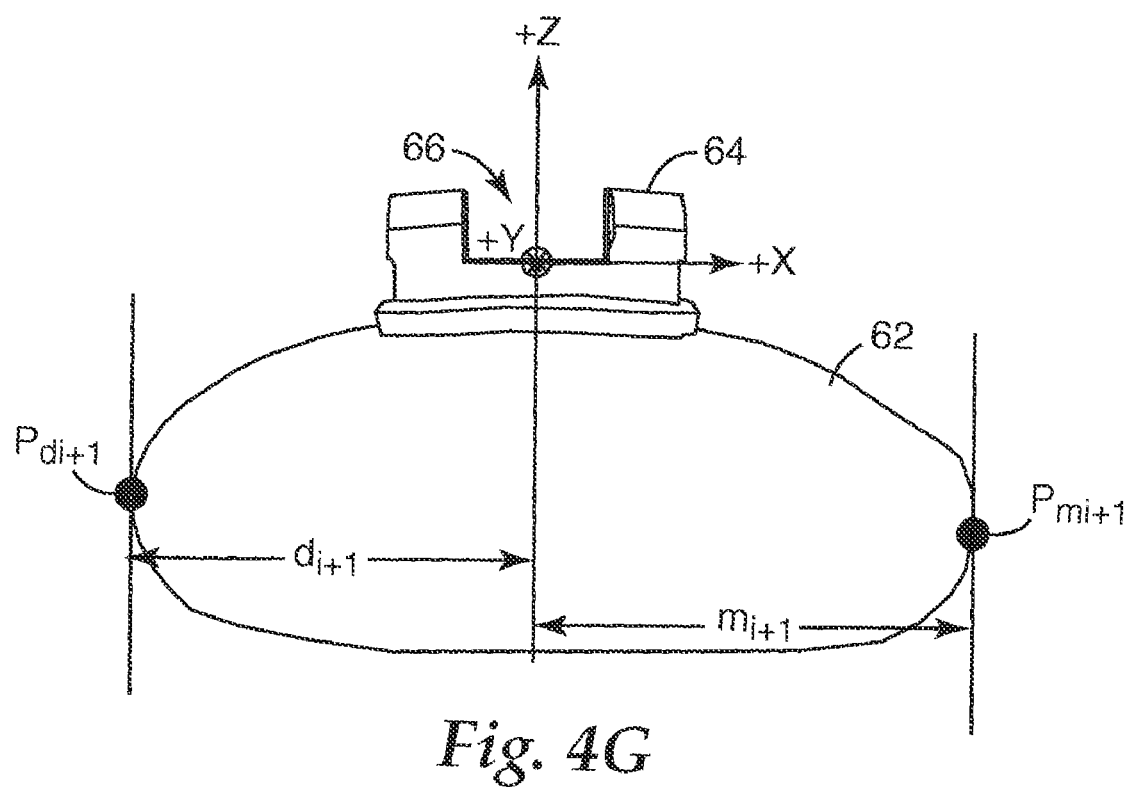

FIG. 4G shows an occlusal view of tooth 62 with the base of bracket 64 in optimal contact with tooth 62. FIG. 4G also shows distal-most point $P_{di+1}$, mesial-most point $p_{mi+1}$, distal distance $d_{i+1}$, and mesial distance $m_{i+1}$. Due to the refit of bracket 64 to tooth 62, distal distance $d_{i+1}$ may no longer approximately equal mesial distance $m_{i+1}$ within the allowable position error $\epsilon$.

For example, referring again to FIG. 3, mesio-distal position control module 24, after calculating distal distance $d_{i+1}$ and mesial distance $m_{i+1}$, determines whether the absolute value of the difference between distal distance $d_{i+1}$ and mesial distance $m_{i+1}$ is less than or equal to allowable position error $\epsilon$ (54). If less than allowable position error $\epsilon$ ("YES" branch 54), mesio-distal position control module 24 makes no further mesio-distal position adjustments and the automatic mesio-distal adjustment process is finished. However, if more than allowable position error $\epsilon$ ("NO" branch 54), mesio-distal position control module 24 continues the automatic mesio-distal adjustment process, as described above.

Throughout the automatic mesio-distal adjustment process, mesio-distal position control module 24 may be programmed to detect one or more conditions that would result in incorrect placement of bracket 64 on tooth 62. One such condition includes instances where, after translation, bracket 64 would intersect or be positioned below a tolerance distance relative to a tooth or bracket adjacent to tooth 62. In these instances, mesio-distal position control module 24 may flag the potential collision with the adjacent tooth or bracket and bring the collision to the attention of practitioner 8. In other embodiments, mesio-distal position control module 24 translates bracket 64 to a position as far as possible along the mesio-distal axis that avoids collision with the adjacent tooth and bracket. In yet another embodiment, mesio-distal position control module 24 translates bracket 64 to a position along the mesio-distal axis but retains some pre-defined distance from the adjacent tooth and/or bracket. The distance may be useful to provide sufficient space to allow for the archwire to be threaded through slot 66 of bracket 64 once applied to the patient.

The automatic mesio-distal adjustment process may occur in any number of ways. In some embodiments, practitioner 8 may place all brackets on each prescribed tooth and then perform the mesio-distal adjustment process. In another embodiment, practitioner 8 may place one bracket on a prescribed tooth, perform the automatic mesio-distal adjustment process, and repeat for each prescribed tooth. In yet another embodiment, practitioner 8 may place one bracket on a prescribed tooth, perform the automatic mesio-distal adjustment process and, simultaneous to performing the automatic adjustment, place another bracket on another prescribed tooth.

Various embodiments of the invention have been described. These and other embodiments are within the scope of the following claims.

The invention claimed is:

1. A computer-implemented method comprising:
rendering at least a portion of a digital representation of a tooth within a three-dimensional (3D) virtual environment;
receiving input from a user quantifying a desired mesio-distal position for a digital representation of an orthodontic appliance associated with the digital representation of the tooth;
determining a distal-most point and a mesial-most point of the digital representation of the tooth within the 3D virtual environment based on an orientation of the digital representation of the orthodontic appliance relative to the digital representation of the tooth within the 3D virtual environment; and
with a computer, executing software to automatically adjust a mesio-distal position of the digital representation of the orthodontic appliance within the 3D virtual environment based on the desired mesio-distal position by at least adjusting the mesio-distal position of the digital representation of the orthodontic appliance based on the determined distal-most point and the determined mesial-most point.

2. The method of claim 1, further comprising displaying the adjusted mesio-distal position of the digital representation of the orthodontic appliance and the digital representation of the tooth within the 3D virtual environment as a visual aid to a practitioner in the placement of the orthodontic appliance on the tooth.

3. The method of claim 1, wherein executing software to automatically adjust the mesio-distal position of the digital representation of the orthodontic appliance further comprises, with the computer, automatically adjusting the mesio-distal position of the digital representation of the orthodontic appliance within the 3D virtual environment relative to a coordinate system associated with the digital representation of the orthodontic appliance.

4. The method of claim 3, wherein executing software to automatically adjust the mesio-distal position of the digital representation of the orthodontic appliance comprises:
with the computer, automatically determining the distal-most point and the mesial-most point of the digital representation of the tooth within the 3D virtual environment relative to the coordinate system associated with the digital representation of the orthodontic appliance.

5. The method of claim 4, further comprising:
prior to determining the distal-most point and the mesial-most point of the digital representation of the tooth, eliminating a set of points that define a surface of the digital representation of the tooth within the 3D virtual environment; and
determining the distal-most point and the mesial-most point from a remaining set of the points.

6. The method of claim 4, wherein executing software to automatically adjust the mesio-distal position of the digital representation of the orthodontic appliance further comprises:
determining a distal-most plane based on the distal-most point and a mesial-most plane based on the mesial-most point; and
with the computer, automatically adjusting the mesio-distal position of the digital representation of the orthodontic appliance within the 3D virtual environment based on the determined distal-most plane and mesial-most plane.

7. The method of claim 6, wherein executing software to automatically adjust the mesio-distal position of the digital representation of the orthodontic appliance further comprises determining a distal distance based on the distal-most plane and a mesial distance based on the mesial-most plane.

8. The method of claim 7, wherein executing software to automatically adjust the mesio-distal position of the digital representation of the orthodontic appliance comprises:
determining a difference between the mesial distance and the distal distance;
comparing the absolute value of the difference to an allowable positional error; and
adjusting the mesio-distal position of the digital representation of the orthodontic appliance within the 3D virtual environment when the difference is greater than the allowable positional error.

9. The method of claim 1, wherein executing software to automatically adjust the mesio-distal position of the digital representation of the orthodontic appliance comprises:
determining a translation distance based on the determined distal-most point and the mesial-most point; and
translating the digital representation of the orthodontic appliance within the 3D virtual environment by the translation distance.

10. The method of claim 9, wherein executing software to automatically adjust the mesio-distal position of the digital representation of the orthodontic appliance comprises determining a mesial distance from an origin of the digital representation of the orthodontic appliance to the mesial-most point within the 3D virtual environment and a distal distance from the origin of the digital representation of the orthodontic appliance to the distal-most point within the 3D virtual environment, and wherein the translation distance is defined as $|m_i-d_i|/2$, wherein m is the mesial distance, $d_i$ is the distal distance and i represents a current iteration of an adjustment to the mesio-distal position of the digital representation of the orthodontic appliance within the 3D virtual environment.

11. The method of claim 9, wherein translating the digital representation of the orthodontic appliance comprises translating the digital representation of the orthodontic appliance by the translation distance along the mesio-distal axis of a coordinate system associated with the digital representation of the orthodontic appliance, wherein the mesio-distal axis extends between the determined distal-most point and the mesial-most point.

12. The method of claim 1, wherein executing software to automatically adjust the mesio-distal position of the digital representation of the orthodontic appliance based on the desired mesio-distal position on the tooth within the 3D virtual environment comprises:
with the computer, executing software to automatically refit the digital representation of the orthodontic appliance to attain a desired fit between a base of the digital representation of the orthodontic appliance and a surface of the digital representation of the tooth within the 3D virtual environment, wherein executing software to automatically refit the digital representation of the orthodontic appliance comprises adjusting the mesio-distal position of the digital representation of the orthodontic appliance relative to the digital representation of the tooth to a refit position within the 3D virtual environment;
after executing software to automatically refit the digital representation of the orthodontic appliance, redetermining the distal-most point and the mesial-most point of the digital representation of the tooth within the 3D virtual environment based on the refit position of the digital representation of the orthodontic appliance; and
after redetermining the distal-most point and the mesial-most point of the digital representation of the tooth within the 3D virtual environment based on the refit position of the digital representation of the orthodontic appliance, executing software with the computer to automatically adjust the mesio-distal position of the digital representation of the orthodontic appliance based on the desired mesio-distal position on the digital representation of the at least the portion of the tooth within the 3D virtual environment based on the redetermined distal-most point and the redetermined mesial-most point.

13. The method of claim 1, further comprising:
rendering a digital representation of a dental arch in which the tooth is one of a plurality of teeth within the 3D virtual environment; and
receiving desired mesio-distal position data for each of the teeth in the dental arch, wherein the desired mesio-distal position data specifies desired mesio-distal positions for orthodontic appliances for each of the teeth.

14. The method of claim 13, wherein each of the teeth in the dental arch has an associated one of the orthodontic appliances, the method further comprising automatically adjusting the mesio-distal position of digital representations of each orthodontic appliance on digital representations of the associated tooth within the 3D virtual environment based on the desired mesio-distal positions.

15. The method of claim 1, wherein receiving input from the user comprises receiving input from a practitioner via a user interface.

16. The method of claim 1, wherein receiving input from the user quantifying a desired mesio-distal position comprises receiving input from the user selecting the desired mesio-distal position from a standardized set of mesio-distal positions.

17. The method of claim 1, wherein the desired mesio-distal position lies along the Facial Axis of the Clinical Crown (FACC).

18. The method of claim 1, wherein the desired mesio-distal position is specified by a customized set of mesio-distal positions.

19. The method of claim 1, wherein the orthodontic appliance comprises an orthodontic bracket, a buccal tube, a sheath, a button or an archwire.

20. The method of claim 1, wherein receiving input from a user quantifying the desired mesio-distal position for the digital representation of the orthodontic appliance associated with the tooth comprises receiving input from a user specifying a numerical offset value from a center of a mesio-distal axis of the digital representation of the tooth within the 3D virtual environment.

21. A system comprising:
a computing device that receives input from a user quantifying a desired mesio-distal position for an orthodontic appliance; and
modeling software executing on the computing device, wherein the modeling software comprises:
a rendering engine that renders at least a portion of a digital representation of a tooth within a three-dimensional (3D) virtual environment; and
a mesio-distal position control module that determines a distal-most point and a mesial-most point of the digital representation of the tooth within the 3D virtual environment based on an orientation of a digital representation of the orthodontic appliance relative to the digital representation of the tooth within the 3D virtual environment, and automatically adjusts a mesio-distal position of the digital representation of the orthodontic appliance within the 3D virtual environment based on the desired mesio-distal position and based on the determined distal-most point and the determined mesial-most point.

22. The system of claim 21, further comprising a user interface to display the adjusted digital representation of the orthodontic appliance and the digital representation of the tooth within the 3D virtual environment.

23. The system of claim 21, wherein the mesio-distal position control module automatically adjusts the mesio-distal position of digital representation of the orthodontic appliance by at least adjusting the mesio-distal position of digital representation of the orthodontic appliance within the 3D virtual environment relative to a coordinate system associated with the digital representation of the orthodontic appliance.

24. The system of claim 23, wherein the mesio-distal position control module automatically adjusts the mesio-distal position of digital representation of the orthodontic appliance by at least determining the distal-most point and the mesial-most point of the digital representation of the tooth within the 3D virtual environment relative to the coordinate system associated with the digital representation of the orthodontic appliance.

25. The system of claim 24, wherein the mesio-distal position control module determines the distal-most point and the mesial-most point of the digital representation of the tooth within the 3D virtual environment by at least:
- eliminating a portion of the points that define the tooth within the 3D virtual environment; and
- determining the distal-most point and the mesial-most point from the remaining points that define the tooth within the 3D virtual environment relative to the coordinate system associated with the digital representation of the orthodontic appliance.

26. The system of claim 24, wherein the mesio-distal position control module automatically adjusts the mesio-distal position of digital representation of the orthodontic appliance by at least further determining a distal-most plane based on the distal-most point and a mesial-most plane based on the mesial-most point.

27. The system of claim 26, wherein the mesio-distal position control module automatically adjusts the mesio-distal position of digital representation of the orthodontic appliance by at least further determining a distal distance based on the distal-most plane and a mesial distance based on the mesial-most plane.

28. The system of claim 27, wherein the mesio-distal position control module automatically adjusts the mesio-distal position of digital representation of the orthodontic appliance by at least further:
- determining a difference between the mesial distance and the distal distance;
- comparing the absolute value of the difference to an allowable positional error; and
- adjusting the mesio-distal position of the digital representation of the orthodontic appliance within the 3D virtual environment when the difference is greater than the allowable positional error.

29. The system of claim 21, wherein the mesio-distal position control module automatically adjusts the mesio-distal position of digital representation of the orthodontic appliance by at least:
- determining a translation distance based on the determined distal-most and mesial-most point; and
- translating the digital representation of the orthodontic appliance within the 3D virtual environment by the translation distance.

30. The system of claim 29, wherein the mesio-distal position control module determines a mesial distance from an origin of the digital representation of the orthodontic appliance to the mesial-most point within the 3D virtual environment and a distal distance from the origin of the digital representation of the orthodontic appliance to the distal-most point within the 3D virtual environment and determines the translation distance according to the equation $|m_i - d_i|/2$, wherein $m_i$ is the mesial distance, and $d_i$ is the distal distance.

31. The system of claim 29, wherein the mesio-distal position control module translates the digital representation of the orthodontic appliance within the 3D virtual environment by at least translating the digital representation of the orthodontic appliance by the translation distance along the mesio-distal axis of a coordinate system associated with the digital representation of the orthodontic appliance, wherein the mesio-distal axis extends between the distal-most point and the mesial-most point.

32. The system of claim 21, wherein the mesio-distal position control module automatically adjusts the mesio-distal position of digital representation of the orthodontic appliance within the 3D virtual environment based on the desired mesio-distal position by at least refitting the digital representation of the orthodontic appliance to attain a desired fit between a base of the digital representation of the orthodontic appliance and a surface of the digital representation of the at least the portion of the tooth within the 3D virtual environment, wherein the mesio-distal position control module refits the digital representation of the orthodontic appliance by at least adjusting the mesio-distal position of the digital representation of the orthodontic appliance relative to the digital representation of the at least the portion of the tooth to a refit position within the 3D virtual environment, and, after refitting the digital representation of the orthodontic appliance, the mesio-distal position control module redetermines the distal-most point and the mesial-most point of the digital representation of the tooth within the 3D virtual environment based on the refit position of the digital representation of the orthodontic appliance and determines whether the digital representation of the orthodontic appliance is at the desired mesio-distal position on the digital representation of the at least the portion of the tooth within the 3D virtual environment based on the redetermined distal-most point and the redetermined mesial-most point of the digital representation of the tooth within the 3D virtual environment.

33. The system of claim 32, wherein if the mesio-distal position control module determines that the digital representation of the orthodontic appliance is not within an allowable position error of the desired mesio-distal position after automatically refitting the digital representation of the orthodontic appliance, the mesio-distal position control module automatically adjusts the mesio-distal position of the digital representation of the orthodontic appliance within the 3D virtual environment based on the desired mesio-distal position and the redetermined distal-most point and the determined mesial-most point.

34. The system of claim 21, further comprising a user interface that receives the input from a practitioner quantifying the desired mesio-distal position, wherein the mesio-distal position control module adjusts the mesio-distal position of the digital representation of the orthodontic appliance within the 3D virtual environment in accordance with the desired mesio-distal position.

35. The system of claim 34, further comprising a database that stores the desired mesio-distal position data for each tooth in the dental arch.

36. The system of claim 34, further comprising a database that stores a set of standardized mesio-distal positions, wherein the user interface receives the input from the practitioner quantifying the desired mesio-distal position by at least receiving input from the practitioner selecting the desired mesio-distal position from the database.

37. The system of claim 36, wherein the database is located remote from the computing device and coupled to the computing device via a network.

38. The system of claim 21, further comprising a database to store data that describes attributes for types of orthodontic appliances that may be selected by the practitioner, wherein the mesio-distal position control module controls the mesio-distal position of the orthodontic appliance based on the stored attributes.

39. The system of claim 21, wherein the desired mesio-distal position lies along the Facial Axis of the Clinical Crown (FACC).

40. A non-transitory computer-readable medium comprising instructions for causing a programmable processor to:
- render at least a portion of a digital representation of a tooth within a three-dimensional (3D) virtual environment;

receive input from a user quantifying a desired mesio-distal position for a digital representation of an orthodontic appliance associated with the digital representation of the tooth;

determine a distal-most point and a mesial-most point of the digital representation of the tooth within the 3D virtual environment based on an orientation of the digital representation of the orthodontic appliance relative to the digital representation of the tooth within the 3D virtual environment;

automatically adjust a mesio-distal position of the digital representation of the orthodontic appliance on the digital representation of the tooth within the 3D virtual environment based on the desired mesio-distal position by at least adjusting the mesio-distal position of the digital representation of the orthodontic appliance based on the determined distal-most point and the determined mesial-most point.

41. A computer-implemented method comprising:

with a computer, rendering at least a portion of a digital representation of a tooth within a three-dimensional (3D) virtual environment;

receiving input from a user indicating a desired mesio-distal position for a digital representation of an orthodontic appliance associated with the tooth;

determining a first distal-most point and a first mesial-most point of the tooth within the 3D virtual environment based on a first orientation of the digital representation of the orthodontic appliance within the 3D virtual environment;

with the computer, automatically adjusting a mesio-distal position of the digital representation of the orthodontic appliance on the digital representation of the tooth within the 3D virtual environment based on the desired mesio-distal position and based on the first distal-most point and the first mesial-most point;

with the computer, automatically refitting the digital representation of the orthodontic appliance to attain a desired fit between a base of the digital representation of the orthodontic appliance and a surface of the digital representation of the tooth, wherein automatically refitting the digital representation of the orthodontic appliance comprises adjusting the digital representation of the orthodontic appliance to a second orientation that is different than the first orientation;

determining a second distal-most point and a second mesial-most point of the tooth within the 3D virtual environment based on the second orientation of the digital representation of the orthodontic appliance; and with the computer, determining whether the digital representation of the orthodontic appliance is within an allowable position error of the desired mesio-distal position on the digital representation of the tooth within the 3D virtual environment based on the second distal-most point and the second mesial-most point of the tooth.

42. The method of claim 41, wherein if the digital representation of the orthodontic appliance is not within the allowable position error of the desired mesio-distal position after automatically refitting the digital representation of the orthodontic appliance, the method further comprises automatically adjusting the mesio-distal position of the digital representation of the orthodontic appliance based on the desired mesio-distal position on the tooth within the 3D virtual environment and based on the second distal-most point and the second mesial-most point.

* * * * *

UNITED STATES PATENT AND TRADEMARK OFFICE
CERTIFICATE OF CORRECTION

PATENT NO.        : 7,940,258 B2                          Page 1 of 1
APPLICATION NO.   : 11/279183
DATED             : May 10, 2011
INVENTOR(S)       : Nicholas Andrew Stark et al.

It is certified that error appears in the above-identified patent and that said Letters Patent is hereby corrected as shown below:

<u>Column 13</u>
Line 8, Claim 10, after "wherein" delete "m" and insert -- $m_i$ --, therefor.

Signed and Sealed this
Thirteenth Day of December, 2011

David J. Kappos
*Director of the United States Patent and Trademark Office*